United States Patent [19]

Pastan et al.

[11] Patent Number: 5,328,984
[45] Date of Patent: Jul. 12, 1994

[54] RECOMBINANT CHIMERIC PROTEINS DELIVERABLE ACROSS CELLULAR MEMBRANES INTO CYTOSOL OF TARGET CELLS

[75] Inventors: Ira H. Pastan, Potomac; Prior Trevor, Bethesda; David J. Fitzgerald, Silver Spring; Waldemar Debinski, Gaithersburg; Clay Siegall, Silver Springs, all of Md.

[73] Assignee: The United States as represented by the Department of Health & Human Services, Bethesda, Md.

[21] Appl. No.: 663,455

[22] Filed: Mar. 4, 1991

[51] Int. Cl.$^5$ .................... C07K 13/00; C07K 15/04; A61K 37/02
[52] U.S. Cl. .................. 424/134.1; 530/402; 530/399; 530/350; 530/387.3; 536/23.4; 435/69.7
[58] Field of Search .............. 424/92, 85.91; 435/69.7; 514/12, 2; 530/350, 402, 391.7; 536/23.4

[56] References Cited

U.S. PATENT DOCUMENTS

| | | | |
|---|---|---|---|
| 4,675,382 | 6/1987 | Murphy | 530/350 |
| 4,892,827 | 1/1990 | Pastan et al. | 424/92 |
| 4,933,288 | 6/1990 | Greenfield | 435/69.5 |
| 5,080,898 | 1/1992 | Murphy | 424/94.6 |
| 5,082,927 | 1/1992 | Pastan et al. | 424/92 |
| 5,084,556 | 1/1992 | Brown | 424/85.91 |
| 5,135,736 | 8/1992 | Anderson et al. | 424/85.91 |
| 5,169,933 | 12/1992 | Anderson et al. | 424/85.91 |
| 5,206,353 | 4/1993 | Berger et al. | 435/69.7 |

OTHER PUBLICATIONS

Lorberbaum-Galski et al., "Interleukin 2 (IL 2) PE40 is Cytotoxic . . . ", *J. Biol. Chem.* 263:18650–18656, Dec. 15, 1988.
Hartley, "Barnase and Barstar", *J. Mol. Biol.* 202:913–915, 1988.
Kondo et al., "Activity of Immunotoxins Constructed with Modified Pseudomonas Exotoxin A . . . ", *J. Biol. Chem.* 263:9470–9475, Jul. 5, 1988.
Batra et al., "Anti-Tac (Fv)–PE40, a Single Chain Antibody Pseudomonas Fusion Protein . . . ", *J. Biol. Chem.* 265:15198–15202, Sep. 5, 1990.
Roberge et al., "Selective Immunosuppression of Activated T Cells . . . ", *J. Immunol.* 143:3498–3502, Dec. 1, 1989.
Prior et al, "Cytotoxic Activity of a Recombinant Fusion Protein . . . ", *Cancer Res.* 51:174–180, Jan. 1, 1991.
Debinski et al., "Substitution of Foreign Protein Sequences into a Chimeric Toxin . . . ", *Mol. Cell. Biol.* 11:1751–1753, Mar. 1991.
Siegall et al., "Cytotoxic Activity of an Interleukin 6–Pseudomonas exotoxin fusion protein . . . ", *PNAS* 85:9738–9742, Dec. 1988.

*Primary Examiner*—Robert A. Wax
*Assistant Examiner*—Stephen Walsh
*Attorney, Agent, or Firm*—Townsend and Townsend Khourie and Crew

[57] ABSTRACT

Proteins that are impermeable and foreign to the eukaryotic cells can now be delivered across cellular membranes into the cytosol of target cells by making a chimeric protein having specific attributes. A method of making such chimeric proteins is disclosed. As an example, a chimeric protein PE-Bar with dual enzymatic activity has been made. The chimeric proteins can be used for cytotoxic, diagnostic or therapeutic purposes, such as for compensating the deficiency or defect of an enzyme or a protein which may be causative of a disease or an abnormality.

13 Claims, 10 Drawing Sheets

☐ PE (1-607)
▨ PE (604-613)
▓ BARNASE (1-110)

| | 1 | 2 | 3 | 4 |
|---|---|---|---|---|
| 200 - | | | | |
| 97 - | | | | |
| 68 - | | | | |
| 43 - | | | | |
| 29 - | | | | |
| 18 - | | | | |

FIG. 3C.

| STRUCTURE OF THE CHIMERIC TOXINS | MOLECULAR WEIGHT (kDa) | PROTEIN SYNTHESIS INHIBITION ASSAY $ID_{50}$ (pM) | |
|---|---|---|---|
| | | A431 CELLS | HT29 CELLS |
| PE — 253 364 381 404 613 | 66 | 106[a] | 303[a] |
| PE40 | 40 | >20,000 | >20,000 |
| TGFα-PE40 — 365 380 N-TERMINUS OF DOMAIN Ib | 46 | 7 | 43 |
| pWD150 — [Thr1]SOMATOSTATIN-14 | 46 | 9 | 52 |
| pWD154 — [Thr1,Ser3,Ser14]SOMATOSTATIN-14 | 46 | 7 | 36 |
| pWD163* — METHIONINE-RICH PEPTIDE | 46 | 10 | |
| pWD148 — DOMAIN Ib AND III OF PE | 69 | 9 | 35 |
| pWD149 — DOMAIN Ib AND III Asp$^{553}$ OF PE | 71 | 17 | 32 |
| pWD151 — DOMAIN Ib AND III OF PE, Asp$^{553}$ | 71 | 22 | 50 |
| pWD152 — Asp$^{553}$ | 46 | 4,000 | >20,000 |

FIG. 8.

RECOMBINANT CHIMERIC PROTEINS DELIVERABLE ACROSS CELLULAR MEMBRANES INTO CYTOSOL OF TARGET CELLS

This invention is related generally to the field of recombinant technology. More particularly, the present invention is related to providing chimeric proteins which render foreign proteins deliverable across cellular membranes into the cytosol of target cells.

BACKGROUND OF THE INVENTION

Chimeric proteins with functions not found in natural proteins are made by fusing diverse DNA elements and expressing the chimeric genes in suitable expression systems. However, it was not known that functional chimeric proteins could be made and expressed, wherein a foreign polypeptide was placed within a host protein. Previous work included addition at the amino or carboxyl termini of natural proteins and involved alterations in the specificity of the binding of the chimeric proteins to the cellular membrane of the target cells. Thus, there was no teaching, suggestion or description in the prior art enlightening and motivating one of ordinary skill in the art of constructing a hybrid protein so that a foreign protein could be delivered across cellular membranes into the cytosol of the host cells. A formidable problem that needed to be considered was the fact that cellular membranes pose a barrier to the translocation of foreign proteins into the cytosol of target cells where the chimeric protein is desired to be introduced and the molecular mechanisms of how some normally internalized proteins reached the cytosol of the cell were not entirely known.

SUMMARY OF THE INVENTION

It is, therefore, an object of the present invention to provide a non-natural hybrid protein a portion of which is translocatable across cellular membranes into the cytosol of the target cells, said hybrid protein containing at least one segment which is a functionally active foreign protein desired to be delivered into the cytosol of the target cells.

An additional object of the present invention is to provide a DNA sequence that encodes a noncytotoxic molecule possessing at least a translocation function and wherein said DNA sequence also has at least a recombinant site for inserting another DNA sequence that encodes a foreign protein or polypeptide. Of course, the DNA sequence may have additional recombinant site(s) for inserting other DNA sequences that encode recognition molecules and convert the noncytotoxic molecule into a cytotoxic entity.

A further object of the present invention is to provide a suitable vector containing a nucleotide sequence that encodes a hybrid protein as defined herein.

It is another object of the present invention to provide a method for making a hybrid foreign protein which can be delivered into the cytosol of the target cells across cellular membranes.

It is a still further object of the present invention to provide a method for introducing an ameliorating, diagnostic or cytotoxic foreign proteins across cellular membrane into the cytosol of target cells.

Other objects and advantages will become evident from the following detailed description of the invention.

BRIEF DESCRIPTION OF THE DRAWINGS

The above and other objects, features and many of the attendant advantages of the invention will be better understood upon a reading of the following detailed description when considered in connection with the accompanying drawings wherein:

FIG. 1 shows a schematic construction of an expression plasmid pTP32f(+)T encoding the Pseudomonas exotoxin barnase chimeric protein, PE-Bar. The plasmid was constructed as described in Materials and Methods: the primers are listed in Table 3.

FIG. 2 is a schematic representation of the domain structure of PE and the barnase toxins. Roman numerals refer to the domains of PE.

FIGS. 3A–3C present the characterization of PE and the barnase toxins. Purified proteins were analyzed using 4–20% (w/v)SDS-PAGE.

(3A) Coomassie blue stained gel (FIG. 3A).

(3B) Immunoblotting with rabbit polyclonal anti-PE antibody (FIG. 3B).

(3C) Immunoblotting with rabbit polyclonal anti-barnase antibody (FIG. 3C).

Lanes 1, PE; lanes 2, PE-Bar; lanes 3 , $PE^{\Delta 553}$-Bar; lanes 4, PE-Bar-COOH. Molecular masses are indicated in kDa.

FIG. 4 shows the inhibition of DNA synthesis by PE and barnase toxins. L929 cells ($3\times10^3$ cells in 0.2 ml) were incubated overnight. Various amounts of PE (○), PE-Bar (●), $PE^{\Delta 553}$-Bar (■) or PE-Bar-COOH (▲) were added to the culture. After 48 hrs. incubation, DNA synthesis was measured. Results are expressed as the % of DNA synthesis activity of the cells incubated without toxin.

FIG. 5 shows the degradation of RNA by PE and barnase toxins in vivo. L929 cells ($1.6\times10^4$ cells in 0.2 ml) were incubated overnight. The cells were incubated with [$^3$H]-uridine for 3 hr. The media was removed and the cells were washed once before replacing with fresh media. PE, PE-Bar or $PE^{\Delta 553}$-Bar were added up to 1000 ng/ml and the cultures incubated for 3 hr. before the amount of uridine-containing macromolecules was measured. Results are expressed as the % of [$^5$H]-uridine in cells incubated without toxin.

FIGS. 6A–6B show the results of treatment of cell lines 103 and 103-PE with barnase toxins. (FIG. 6A) 103 and (FIG. 6B) 103-$PE^R$ cells were prepared as described in the legend to FIG. 5. Various amounts of PE (●), or PE-Bar (■) were added to the culture. After 48 hrs. incubation, protein synthesis was measured. Results are expressed as the % of protein synthesis activity of cells incubated without toxin.

FIGS. 7A–7C show SDS-polyacrylamide gel electrophoresis and immunoblots of additional chimeric proteins. (FIG. 7A) SDS-PAGE followed by staining with Coomassie blue. (FIGS. 7B and 7C) show the corresponding immunoblots. Anti-PE antibody was used in (FIG. 7B) and anti-somatostatin antibody was employed in (FIG. 7C). For each gel, lane: 1) TGFα-PE40 (pWD156); 2) -PE40[Thr1]somatostatin-14 (pWD150); 3) TGFα-PE40 [Thr1, Ser3, Ser14]somatostatin-14 (pWD154): 4) TGFα-PE40$Asp^{553}$ (pWD152); 5) TGFα-PE40 methionine-rich peptide (pWD163); 6) TGFα-PE40 domain III (pWD148); 7) TGFα-PE40$Asp^{553}$ domain III (pWD149); 8) TGFα-PE40 domain III$Asp^{553}$ (pWD151).

FIG. 8 shows schematic representation of PE, PE40 and additional chimeric toxins, and their cytotoxicity on A431 and HT29 cells. Solid lines correspond to PE sequences. The numbers at the vertical bars indicate amino acids as present in PE. The dotted line represents domain I of PE (amino acid 1-253)—not drawn to scale. Open boxes at the N-terminus represents the TGFα molecule. PE40 contains domain II ($Gly^{253}$-$Asn^{364}$), domain Ib ($Ala^{365}$-$Gly^{404}$) and domain III ($Gly^{405}$-$Lys^{613}$) of PE. The sequences of substitutions in N-terminus of domain Ib (SEQ ID NO: 1) (ADVVSLTC-PVAAGECA) were as follows: (SEQ ID NO:2) TGCKNFFWKTFTSC for Somatostatin-14 in pWD150; SEQ ID NO:3) TGSKNFFWKTFTSS for Somatostatin-14 in pWD154; (SEQ ID NO:4) MDMMMMTCPMMMGTCM for methionine-rich peptide in pWD163; $Gly^{381}$-$Lys^{613}$ of PE in pWD148; $Ala^{365}$-$Lys^{613}$ of PE with $Glu^{553}$ to Asp mutation in pWD149; $Ala^{365}$-$Lys^{613}$ of PE in pWD151. Purification on Mono-Q column or by gel filtration.

DETAILED DESCRIPTION OF THE INVENTION

Figure 1:
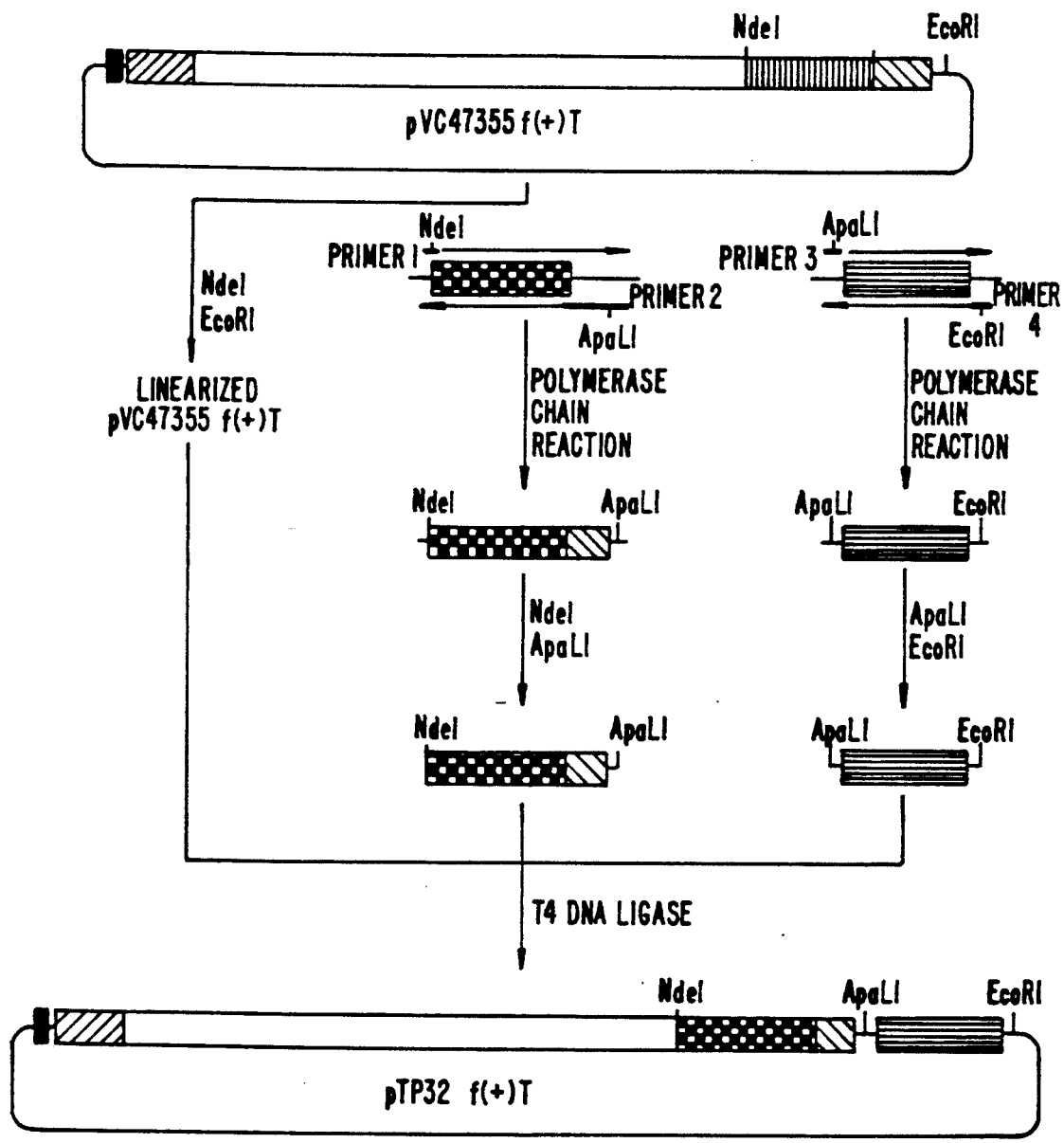

The above and various other objects and advantages of the present invention are achieved by (1) providing a recombinant molecule possessing at least a recognition element, a translocation function and one or more recombinant sites for inserting foreign proteins or polypeptides, and (2) making a recombinant chimeric protein translocatable across cellular membranes into the cytosol of target cells, said chimeric protein having at least one segment which is a functionally active foreign protein desired to be introduced de novo into the cytosol of the target cells, a recognition element that directs the hybrid protein to the target cells, and an additional segment having at least a translocation function which internalizes the protein and delivers the foreign protein into the cytosol of the target cells. In case of PE, the recombinant sites could be located in either or both of domains Ib or III, but not in domain II.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The term "substantially pure" as used herein means that the protein is obtained as free of impurities as it is possible to make by standard isolation and purification techniques.

The term "chimeric" or "hybrid" protein as used herein means a fusion protein made by recombinant technology that contains a foreign protein as its integral part.

The term "target" or "host" cells as used herein means specific eukaryotic cells or cell types into the cytosol of which the chimeric protein needs to be delivered selectively, that is, to the exclusion of all other cells or cell types.

The term "foreign" protein as used herein means a protein that is desired to be delivered in the cytosol of the target cell and which is either absent, deficient or defective in the target cell and that, by itself, cannot reach the cytosol of the target cell. Such foreign proteins include an enzyme, a marker protein, a diagnostic, therapeutic or a cytotoxic moiety and the like.

The term "recognition molecule", "recognition ligand" or "recognition element" as used herein means a protein, a ligand, a growth factor or the like which selectively recognizes or binds to target cells at the exclusion of all other cells.

The term "translocatable" as used herein means that the molecular entity, which by itself cannot cross the cellular membrane, however, becomes deliverable across cellular membrane by becoming a part of the chimeric protein.

The term "PE" as used herein means a natural or any modified form of PE including deletion, addition, substitution or mutation in the PE molecule, whether by recombinant technology or otherwise.

The term "recombinant site" as used herein means a site deliberately created by recombinant technology where the foreign protein is introduced to make the hybrid protein, said site being in a location other than the conventionally recognized translocation domain of the host molecule (such as domain II of PE).

In order to demonstrate the general principles of the present invention, two components were chosen. The first component was a natural or modified form of the Pseudomonas exotoxin A (PE). The three dimensional structure of PE is known and the functions of various domains of PE have been established. It was found that domain Ia is responsible for cell recognition and binding, domain II for translocation across the cell membrane and domain III for the ADP-ribosylating activity. Unmodified PE enters the cell via receptor-mediated endocytosis and is translocated into the cytosol where it catalyzes the ADP-ribosylation of elongation factor-2(EF-2) which leads to cell death. Only a 37 kDa protein fragment from the carboxyl end of the toxin is translocated to the cytosol (Ogata et al, 1990, J. Biol. Chem. 265:20678–20685). It was recently demonstrated that by deleting the cell recognition domain Ia, a 40 kDa protein (termed PE40) is produced (Kondo et al, 1988, J. Biol. Chem, 263:9470–9475) which is not cytotoxic to cells despite retaining the translocation and ADP-ribosylation functions (domain II and III). Hence, by replacing or modifying domain Ia, a number of chimeric toxins of differing specificities have been produced (see Pastan et al, 1989, J. Biol. Chem. 264:15157–15160). Because of the various known properties of PE, this protein in its natural or modified form was chosen as one of the components of the novel hybrid protein of the present invention about to be described fully herein infra. Of course, any other entity which has translocating property such as possessed by PE, could also be used as a translocating vehicle.

The second component of the hybrid protein of the present invention is a foreign protein which normally would not enter the cytosol due to the permeability barrier posed by cellular membranes, but which is intended to be introduced into the cytosol for its desired therapeutic, diagnostic, ameliorating or cytotoxic property and the like. Barnase was chosen herein for illustrative purposes only.

Barnase is an extracellular ribonuclease produced by *Bacillus amyloliquefaciens* (*B. amyloliquefaciens*) (for review see Hartley, 1989, Trends Biochem. Sci. 14:450–454). The protein is synthesized as a proenzyme and the secreted, native form of barnase is small (110 amino acids), thus facilitating physical studies, including determination of its three-dimensional structure to 2 Å (Mauguen et al, 1982, Nature 297:162-164). In *B. amyloliquefaciens*, the intracellular activity of barnase is inhibited by a specific inhibitor termed barstar (Smeaton and Elliot, 1967, Biochem. Biophys. Acta 145:547-560; Hartley and Smeaton, 1973, J. Biol. Chem. 248:5624-5626). Early attempts to express active barnase in *E. coli* were unsuccessful due to the degradation of intracellular RNA that killed the microorganism. However, this problem was overcome by cloning the structural genes for barnase and barstar on the same plasmid (Hartley, 1988, J. Mol. Biol. 202:913-915). Since some toxins, for example ricin, exert their cytotoxic effects by the modification of ribosomal RNA (Endo et al, 1987, J. Biol. Chem. 262:5908-5512)), we set out to determine whether the ribonuclease activity of barnase could be introduced into the cytosol, digest RNA and function as a chimeric toxin. It was reasoned that if success were achieved, it would open a new avenue for constructing novel, translocatable hybrid proteins possessing a plurality of needed functions, such as marker or diagnostic activity, two or more enzymatic functions, enhanced or different cytotoxic activities and the like.

Illustrated herein now is the construction, expression, purification and activities of chimeric fusion proteins composed of PE and barnase. These proteins contain both ribonuclease and ADP-ribosylating activity. It was indeed unexpected to find that the chimeric toxins are cytotoxic to a murine fibroblast cell line even when the ADP-ribosylating activity is eliminated by mutation.

MATERIALS AND METHODS

Reagents

Unless indicated otherwise, all chemicals and enzymes were purchased from commercial sources. Rabbit polyclonal serum to barnase was a gift from Dr. R. W. Hartley, National Institutes of Health. The Gene-Amp Polymerase Chain Reaction (PCR) kit was purchased from United States Biochemcial Corp. (Cleveland, Ohio). Ethenoadenosine diphosphate and polynucleotide phosphorylase were purchased from Sigma Chemical Corp. (St. Louis, Mo.). [$^3$H]-uridine (37.5 Ci/mmol) and [$^3$H]-thymidine (6.7 Ci/mmol) were from NEN/Dupont (Boston, Mass.), [$^3$H]-leucine 125 Ci/mmol) was purchased from Amersham Corp. (Arlington Heights, Ill.).

Plasmids, Bacterial Strains and Cell Lines

Plasmid pVC47355 f(+)T carries the DNA encoding the chimeric toxin PE-TGFα and was designed such that the DNA encoding transforming growth factor alpha (TGFα) is bounded by NdeI sites at both the 5' and 3' ends. The cDNA for this growth factor is preceded by amino acids 1-607 and followed by amino acids 604-613 of PE. Plasmid pMT416, containing the DNA encoding barnase and barstar (Hartley, 1988, supra), was a gift from Dr. R. W. Hartley, *E. coli* strain BL21 (λDE3) has been described previously (Studier and Moffatt, 1986, J. Mol. Biol. 189:113-130). L929 is a murine fibroblast cell line. Cell line 103-PE ® is a PE-resistant subclone of the murine hybridoma OVB3 (Willingham et al, 1987, Proc. Natl. Acad. Sci. USA 84:2474-2478) which has a mutation in EF-2 such that it can no longer be ADP-ribosylated by PE.

Plasmid Construction

Oligonucleotides were prepared as described previously by Lorberboum-Galaki et al, 1988, Proc. Natl. Acad. Sci. USA 85:1922-1926. Plasmid DNA was prepared also as described by Lorberboum-Galski et al, 1988, supra, or by using QIAGEN columns (QIAGEN, Inc., Studio City, Calif.) according to the manufacturer's instructions. The chimeric gene encoding PE-barnase (PE-Bar) under the control of the bacteriophage T7 promoter was constructed as shown in FIG. 1. This plasmid also contains the DNA encoding barstar, which is transcribed from the same promoter as a polycistronic message. The gene fragment encoding barnase was prepared using PCR (Saiki et al, 1985, Science 230:1350-1354; Scharf et al, 1986, Science 233:1076-1078) from plasmid pMT416 using (SEQ III NOS: 5 and 6) primers 1 and 2 (Table 3). (SEQ ID NO: 5) primer 1 is complementary to the 3' region of the antisense strand of the barnase DNA and has an NdeI recognition site (SEQ ID NO: 6). Primer 2 is complementary to the 3' region of the sense strand of the barnase DNA. In addition, this primer also contains DNA encoding the carboxyl end of PE (amino acids 604-613) and for an ApaLI restriction site. Use of these primers resulted in no changes to the primary sequence of barnase. The gene fragment encoding barstar was prepared using PCR amplification of plasmid pMT416 using primers 3 and 4: primer 3 (SEQ ID NO: 7) is complementary to the 3' region of the antisense strand of the barstar DNA, and (SEQ ID NO: 8) primer 4 is complementary to the 3' region of the sense strand of the barstar DNA. Amplification using (SEQ ID NO: 7) primer 3 resulted in the introduction of an ApaLI recognition site, followed by a Shine-Dalgarno sequence (AA-GAGG) and the initiation codon ATG. Use of (SEQ ID NO: 8) primer 4 resulted in the introduction of an EcoRI site immediately after the translation stop codon (TAA) of barstar with no change in the sequence of barstar. Amplification of a 414 base pair (bp) fragment of barnase and the carboxyl end of PE was accomplished after 30 cycles of PCR using (SEQ ID NO: 5) primer 1 (SEQ ID NO: 6) and primer 2 (1 μM each) and 10 ng of plasmid pMT416 as the template. Similarly, use of (SEQ ID NO: 7) primer 3 and (SEQ ID NO: 8) primer 4 resulted in the amplification of a 324 bp fragment encoding barstar. After purification on 1.5% (w/v) low-melting point agarose (SeaPlaque GTG Agarose, FMC Bioproducts, Rockland, Me.) the amplified fragments were digested with NdeI and ApaLI (for barnase) and ApaLI and EcoRI (for barstar). The resulting 381 bp and 294 bp (respectively) DNA fragments were purified from low-melting point agarose. Plasmid pVC47355 f(+)T was prepared by digestion with NdeI and EcoRI. The 4.9 kb band was separated and purified from a 1% (w/v) low-melting point agarose gel. The DNA fragments were ligated and the recombinants screened by standard restriction digestion analysis. Several positive clones were checked for protein expression. Plasmid pTP32 f(+)T was identified as carrying the gene for the chimeric toxin PE-Bar.

Plasmid pTP36 f(+)T, encoding a mutant form of PE-Bar lacking amino acids 604-613 of PE, was prepared exactly as above except that (SEQ ID NO: 5) primer 5 replaced (SEQ ID NO: 6) primer 2 in the PCR amplification of barnase. (SEQ ID NO: 9) Primer 5 introduced a stop codon (TAA) immediately after the last amino acid of barnase, and an ApaLI restriction site.

The protein expressed from this plasmid, designated PE-Bar-COOH, lacks the essential carboxyl terminus amino acids required for cytotoxicity (Chaudhary et al, 1990, Proc. Natl. Acad. Sci. USA 87:308-312).

Plasmid pTP42 f(+)T, encoding PE$^{\Delta 553}$-Bar, was prepared as follows. Plasmid pTP32 contains a KpnI recognition site in the DNA encoding for domain I of PE, and a PvuII recognition site in the DNA encoding for barstar. In addition, there are several NarI recognition sites; there is, however, only one NarI site between the KpnI and PvuII sites in the PE coding region. This NarI site is located in domain III of PE immediately upstream of the codon encoding for glutamic acid 553. The deletion of amino acid 553 was accomplished using PCR amplification from plasmid pTP32 f(+)T using (SEQ ID NO:10) primer 6 and (SEQ ID NO:11) primer 7. (SEQ ID NO:10) Primer 6 is complementary to the 3' region of the antisense strand of the DNA encoding the carboxyl terminus of PE-Bar, and includes the NarI site. In addition (SEQ ID NO:10), primer 6 was synthesized lacking the codon encoding Glu$^{553}$, resulting in its deletion from the amplified product. (SEQ ID NO:11) Primer 7 is complementary to the 3' region of the sense strand of the DNA encoding barstar, and includes the PvuII recognition site. The amplified DNA fragment encoding the carboxyl terminal of PE-Bar, deleted of amino acids Glue $^{553}$, and the amino terminal of barstar was amplified and purified as described above. The fragment was prepared for ligation by digestion with NarI and PvuII. Two restriction fragments were prepared from plasmid pTP32 f(+)T. The first was a 1323 bp KpnI-NarI fragment encompassing the carboxyl end of domain I, domain II and the amino terminal end of domain III. The second was a 3.5 kb KpnI-PvuII fragment which contained the vector DNA and the DNA encoding for the amino terminal of PE-Bar, and the carboxyl terminal of barstar. These two fragments were ligated with the prepared PCR-amplified fragment and the resulting recombinants were analyzed as described herein above.

Protein Expression and Purification

The chimeric toxins were prepared using *E. coli* strain BL21 (λDE3). All of the constructions used in this study contained the OmpA signal peptide, consequently the expressed proteins were secreted into the periplasm. After induction with isopropyl-β-D-galactopyranoside (IPTG), the chimeric toxins were purified using Q-Sepharose fast-flow and Mono-Q (Pharmacia LKB Biotechnology Inc., Piscataway, Pa.) anion-exchange chromatography, followed by gel filtration on a TSK-G3000 SW column as described previously (Siegall et al, 1988, Proc. Natl. Acad. Sci. USA 85:9738-9742). Since barstar binds tightly to barnase, it was necessary to separate these proteins. Consequently, the TSK-G3000 SW purified material was denatured in 7M guanidine-hydrochloride, 5 mM EDTA, 100 mM Tris-HCl pH 8.0 and loaded onto a TSK-G3000SW column previously equilibrated with this solution. The larger PE-Bar was separated from the smaller barstar by this procedure. The chimeric toxin was renatured by rapid dilution into 50 volumes cold phosphate-buffered saline and stirred overnight (about 12-16 hrs) at 4° C. The solution was diluted 10-fold in 20 mM Tris HCl pH 7.4, 1 mM EDTA (Buffer A), loaded onto a 1 ml Mono-Q anion exchange column, and eluted using a linear gradient 0-500 mM NaCl in buffer A (data not shown). The substantially pure protein eluted as a single peak at 250 mM NaCl.

Gel Electrophoresis and Immunoblotting

Sodium dodecylsulfate (SDS) polyacrylamide gel electrophoresis (PAGE) was performed using 4-20% (w/v) gradient gels (NOVEX Inc., Encinitas, Cailf.) as described by Laemmli, 1970, Nature 227:680-685). For Western blotting, electrophoresed samples were transferred onto nitrocellulose paper and immunoblotted as described by Hwang et al, 1987, Cell 48:129-136, using rabbit anti-PE antiserum or rabbit anti-barnase antiserum.

Protein Synthesis Inhibition Assay

The cytotoxicity of the chimeric toxins was tested on L929 cells using two methods. The first was an inhibition of protein synthesis assay. Cells were placed in 96-well tissue culture dishes at $3 \times 10^3$ cells per well for 24 hours before assaying. The toxins were diluted in PBS containing 0.2% (w/v)human serum albumin and added at various concentrations to the cells. After incubation for various times (for example 48 hours) at 37° C. in 5% $CO_2$ the cells were cultured with [$^3$H]-leucine (1.0 μCi) for 3 hours. The cells were harvested by filtration onto glass fiber membranes (Skatron 12-well harvester or TomTec 96-well harvester) and the rate of [$^3$H]-leucine incorporation determined (BetaPlate Scintillation Counter, Pharmacia/Wallac Ltd, Gaithersburg, Md.).

DNA Synthesis Inhibition Assay

The second assay for cytotoxicity was an inhibition of DNA synthesis assay. This assay was performed exactly as described above except that [$^3$H]-thymidine (0.2 μCi) was added to the cells.

In vivo RNase Assay

The ability of the toxins to degrade intracellular RNA was measured as follows. Cells were plated in 96-well tissue culture dishes at $1.6 \times 10^4$ cells per well 24 hours prior to assaying. [$^3$H]-uridine (1.0 μCi) was added to the cells for 3 hours; the media was removed and the cells washed twice in media prior to the addition of toxin at 1000 ng/ml. The cells were incubated for a further 3 hours and the amount of radioactivity incorporated by the cells in macromolecular compounds was determined by filtration and scintillation spectroscopy as described above.

In vitro RNase Assay

Ribonuclease activity was determined by a standard fluorometric assay by measuring the degradation of polyethenoadenosine phosphate.

ADP-ribosylation Activity

ADP-ribosylation was measured using a wheat germ extract as the source of EP-2 as described previously by Hwang et al, 1987, supra.

RESULTS

Construction of An Expression Plasmid Encoding PE-Bar and Derivatives

Figure 2:
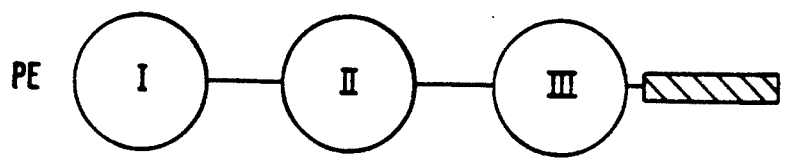
Figure 2:
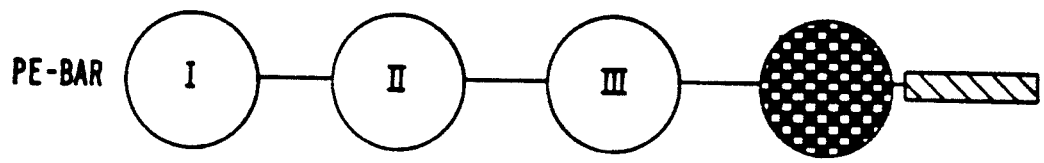
Figure 2:
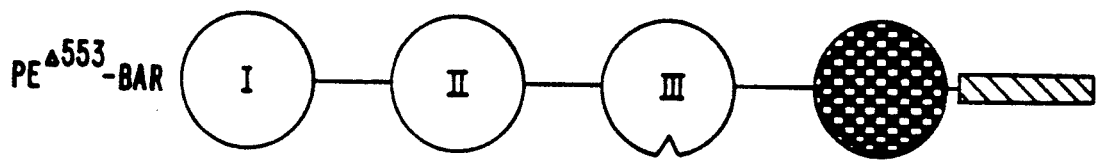
Figure 2:
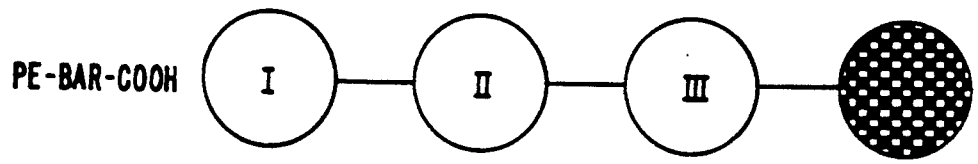

A DNA fragment encoding the mature form of barnase was inserted into the DNA sequence encoding the carboxyl terminal region of PE (FIG. 1). DNA encoding the barnase inhibitor, barstar, was inserted between the stop codon of the chimeric toxin and the transcription terminator. The 758-residue chimeric protein, PE-Bar, is composed of the OmpA signal sequence, amino acids 1–607 of PE fused to amino acids 1–110 of mature barnase and, finally, amino acids 604–613 of PE. In a similar fashion, the genes encoding the chimeric proteins PE$^{\Delta 553}$-Bar, which lacks amino acid 553 (glutamic acid) of PE and therefore has no ADP-ribosylating activity, and PE-Bar-COOH, which lacks amino acids 604–613 of PE required for translocation of PE into the cytosol (Chaudhary et al, 1990, supra) were prepared. A schematic representation of the proteins encoded by these genes is shown in FIG. 2.

A deposit of pTP42 encoding PE$^{\Delta 553}$-Bar [also designated alternatively as pTP42 f(+)T] has been made under Budapest Treaty at the ATCC, Rockville, Md. on Jan. 29, 1991 under the accession number 68521. The deposit shall be viably maintained, replacing if it becomes non-viable during the life of the patent, for a period of 30 years from the date of the deposit, for 5 years from the last date of request for a sample of the deposit, whichever is longer, and upon issuance of the patent made available to the public without restriction in accordance with the provisions of the law. The Commissioner of Patents and Trademarks, upon request, shall have access to the deposit.

Expression and Purification of the Chimeric Toxins

Figure 3A:
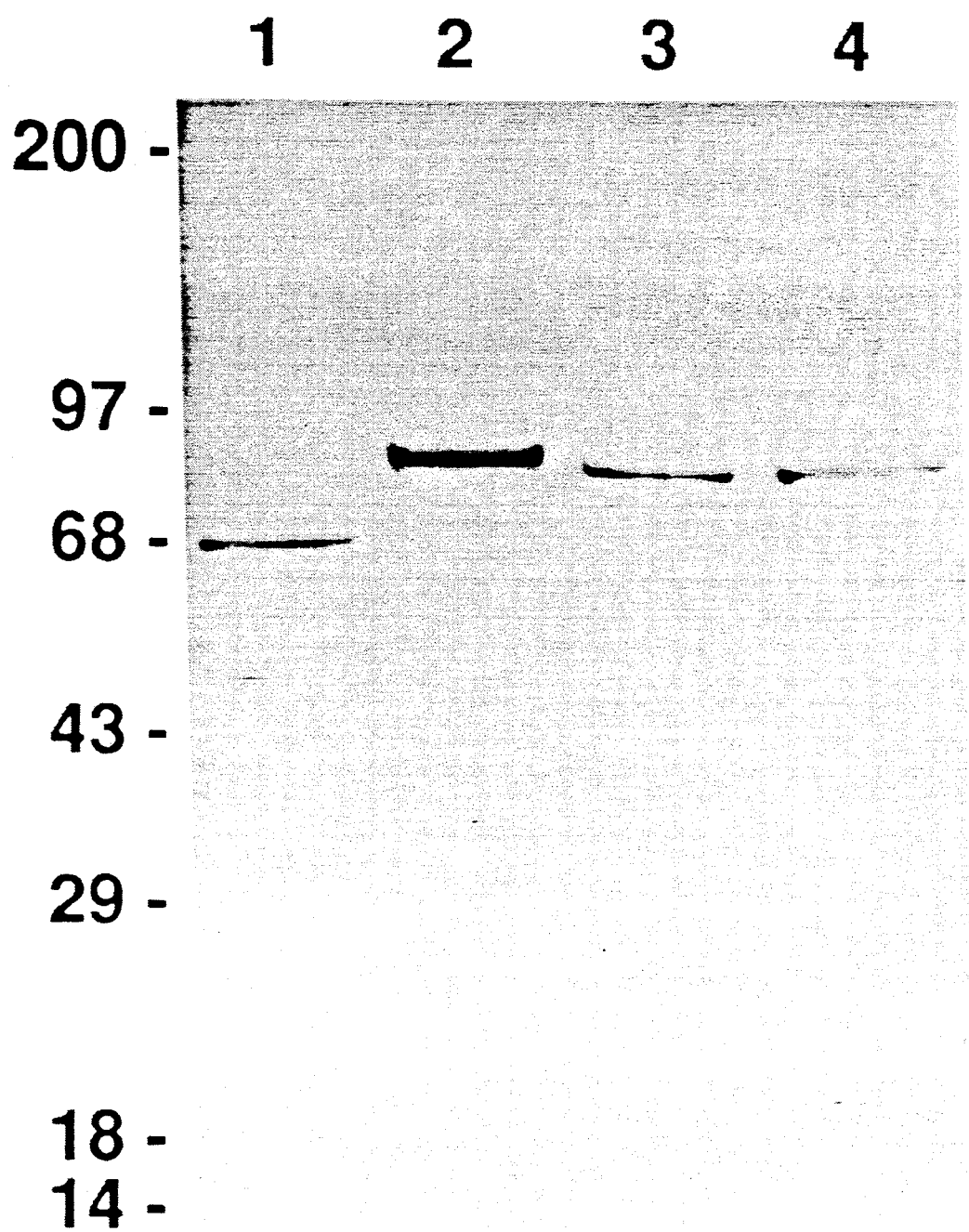
Figure 3B:
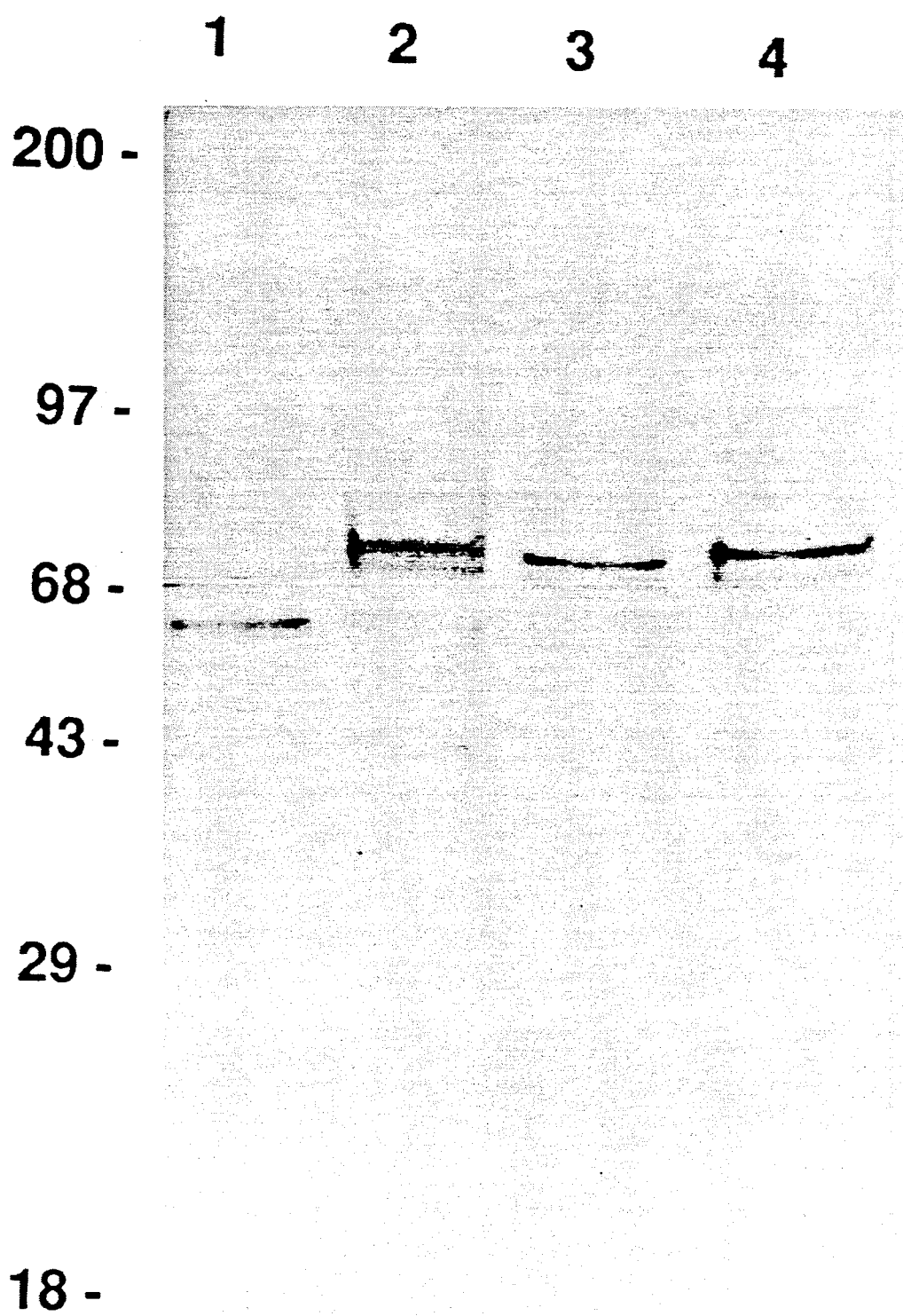
Figure 3C:
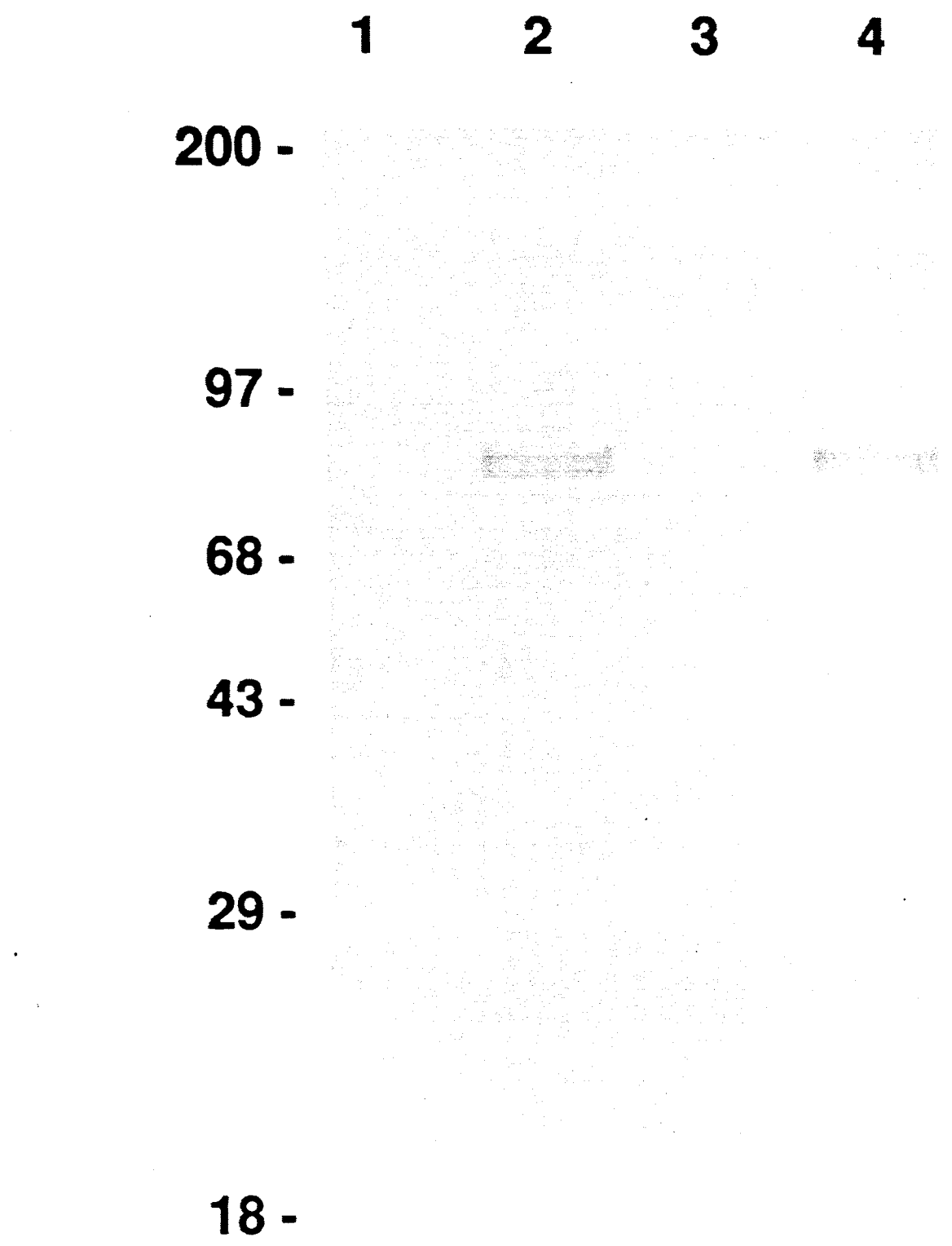

The chimeric toxins were expressed by cultures of *E. coli* strain BL21 ($\lambda$DE3). Since the genes contained the OmpA signal sequence, induction with IPTG resulted in the appearance of the expressed protein in the periplasm. These expressed proteins migrated on SDS-PAGE with an apparent molecular mass of approximately 72 kiloDaltons (kDa) corresponding to the expected molecular mass of PE-Bar, and reacted with anti-PE antiserum (data not shown). The chimeric toxins were purified from this source. The initial purification steps included chromatography over Q-Sepharose Fast-Flow and Mono-Q anion exchange columns, and gel filtration over a TSK G3000SW sizing column. The proteins eluted at positions expected for PE proteins (data not shown). Since barstar binds tightly to, and copurifies with, barnase, it is necessary to chaotropically separate the two proteins (Hartley, 1989, Trends Biochem. Sci. 14:450–454). Thus, the gel filtration purified fraction was treated with guanidine hydrochloride and loaded onto a second TSK G3000SW column previously equilibrated with buffer containing guanidine hydrochloride. The elution profile showed two peaks of absorbing (280 nm) activity (data not shown). The first peak, corresponding to PE-Bar, was renatured in PBS (Siegall et al, 1988, supra) and, after dilution to reduce the salt concentration, loaded onto a MonoQ anion exchange column. A single peak, identified as PE-Bar, eluted at 250 mM NaCl, and was greater than 95% pure, as determined by SDS-PAGE (FIG. 4A). As shown in FIG. 3B and 3C, the chimeric toxins PE-Bar, PE$^{\Delta 553}$ and PE-Bar-COOH all reacted with both anti-PE (FIG. 3B) and anti-barnase (FIG. 3C) antisera. Of course, PE reacted only with anti-PE antiserum.

Enzymatic Activity of the Chimeric Toxins

Since the chimeric toxins were composed of proteins having distinct enzymatic activities, the presence of ADP-ribosylation and ribonuclease activity in the toxins was determined. Both PE-Bar and PE-Bar-COOH had ADP-ribosylation levels (90% and 80%, respectively) comparable to that seen with PE (Table 1). As expected, the mutant protein PE$^{\Delta 553}$-Bar had no ADP-ribosylation activity.

The ribonuclease activity of the recombinant proteins also was determined (Table 1). Corrected for the differences in molecular mass between barnase (12.5 kDa) and the chimeric toxins (78.5 kDa), the proteins, respectively, PE-Bar, PE$^{\Delta 553}$-Bar and PE-Bar-COOH had 80%, 50% and 68% of the ribonuclease activity of native barnase. PE had no (<0.1%) measurable ribonuclease activity. Thus, the chimeric toxin possesses both ribonuclease and ADP-ribosylation activities in a single polypeptide chain.

Cytotoxic Activity of the Chimeric Toxins

Figure 4:
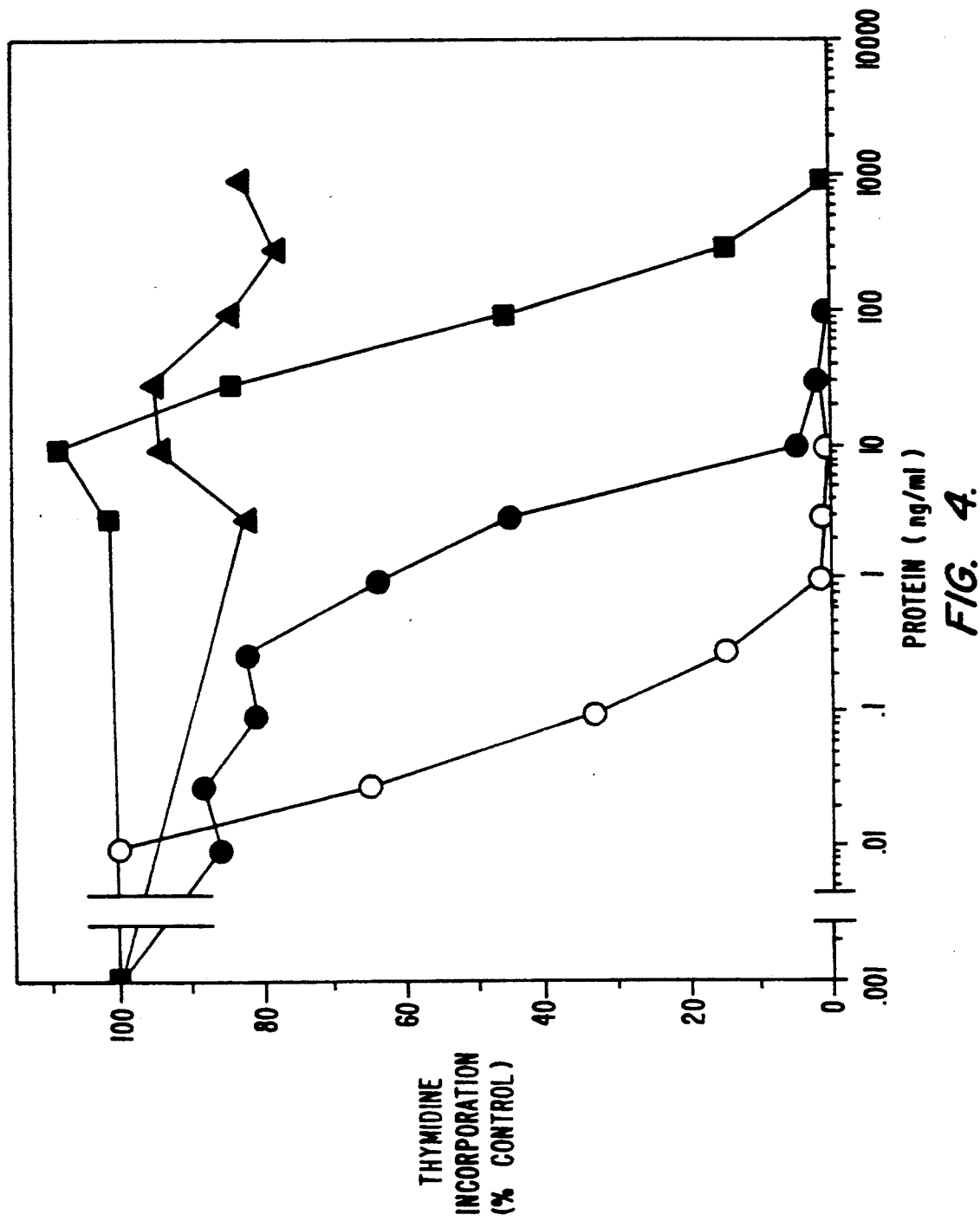

The cytotoxic activity of the various PE-Bar constructions was evaluated on the murine fibroblast cell line L929. The cells were incubated for 48 hours with varying amounts of toxin and the rate of DNA synthesis measured to assess the cytotoxic activity of the proteins. As shown in FIG. 4, PE and the chimeric toxins PE-Bar and PE$^{\Delta 553}$-Bar, inhibited DNA synthesis in L929 cells. The concentration of toxin giving a 50% inhibition of DNA synthesis (ID$_{50}$) was 0.05 ng/ml, 2 ng/ml and 90 ng/ml for PE, PE-Bar and PE$^{\Delta 553}$-Bar, respectively. PE-Bar-COOH, which lacks the carboxyl terminal of PE, had no detectable effect on DNA synthesis (ID$_{50}$>1000 ng/ml). Table 2 shows the results of similar experiments in which the cells were incubated with the toxins PE-Bar and PE$^{\Delta 553}$-Bar for 24 hours. The ID$_{50}$'s decreased from 9 ng/ml for PE-Bar and 150 ng/ml for PE$^{\Delta 553}$-Bar at 24 hours to 2 ng/ml and 90 ng/ml, respectively, after 48 hours.

The cytotoxicity of the toxins was evaluated also by measuring their ability to inhibit protein synthesis (Table 2). After 48 hours, PE-Bar had an ID$_{50}$ of 5 ng/ml, and PE$^{\Delta 553}$-Bar had an ID$_{50}$ of 60 ng/ml on L929 cells. Thus, the proteins were toxic to the target cells even in the absence of ADP-ribosylation activity.

Effect of Chimeric Toxins on Prelabeled RNA In Vivo

Figure 5:
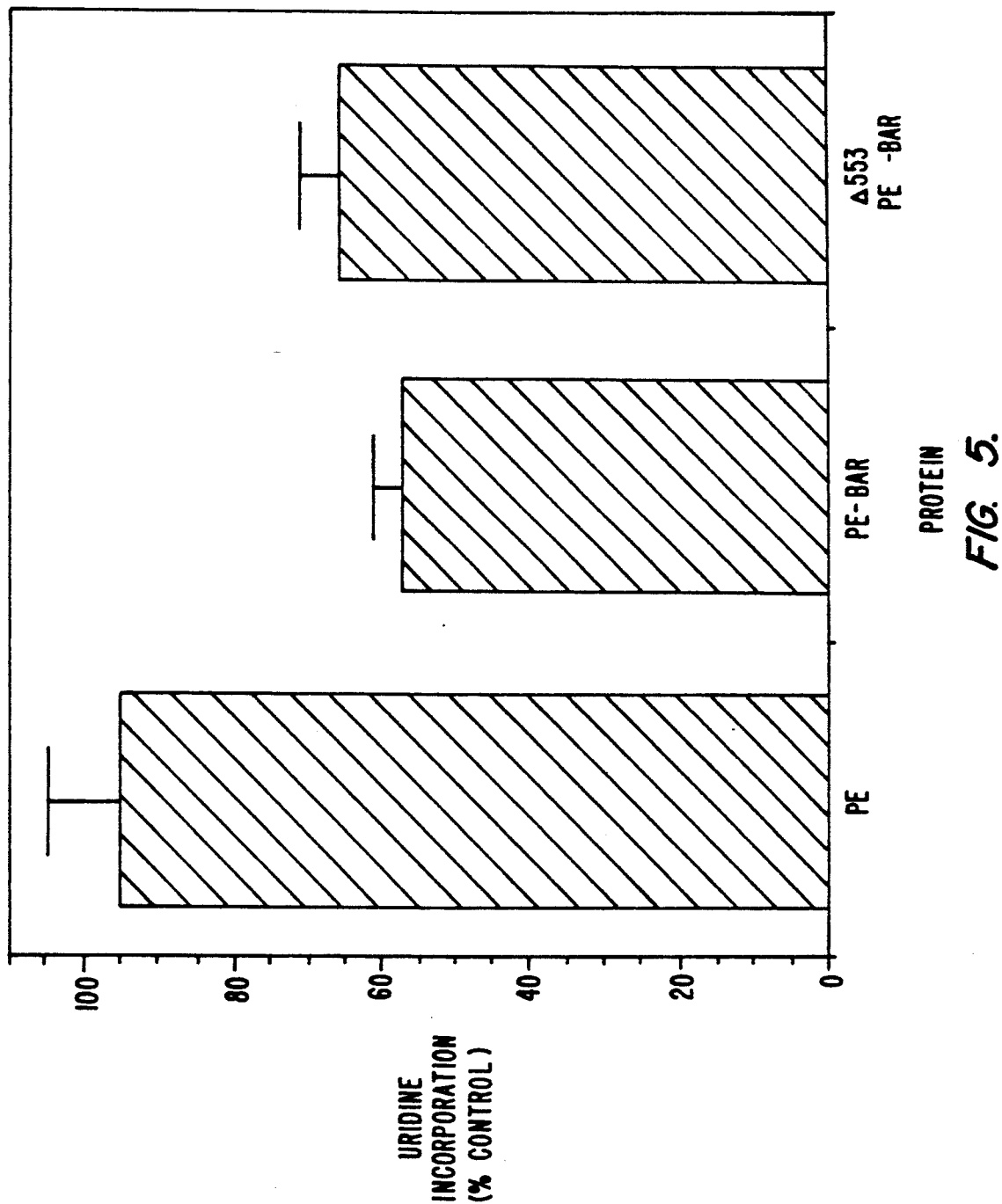

To demonstrate that the ribonuclease function of barnase was active and responsible for the cytotoxicity observed with PE$^{\Delta 553}$-Bar, the degradation of RNA in treated cells was measured. L929 cells were prelabeled with radiolabeled uridine and treated with toxin for 3 hrs as described earlier. The results (FIG. 5) show a decrease in the amount of radiolabeled uridine present in RNA in cells treated with PE-Bar (57%±4% of control) or PE$^{\Delta 553}$-Bar (66%±5%), but not in cells treated with PE (95%±10%).

Effect of Chimeric Toxins on a PE-resistant Cell Line

Figure 6A:
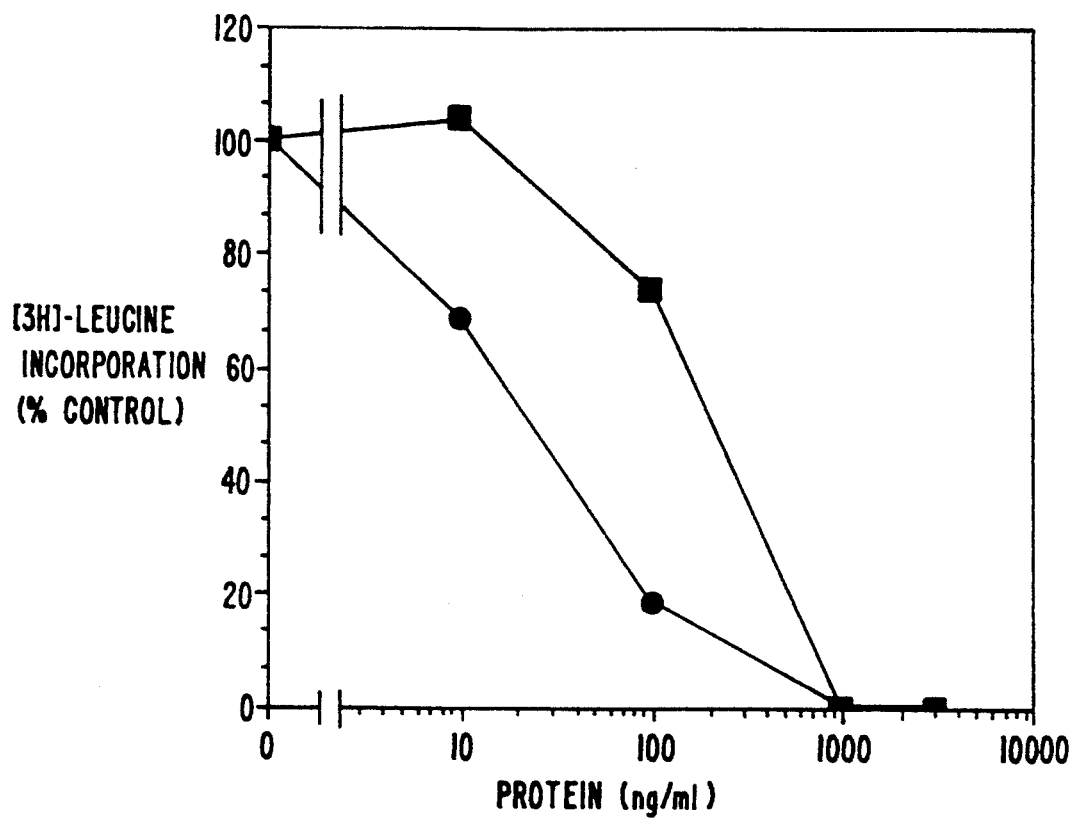
Figure 6B:
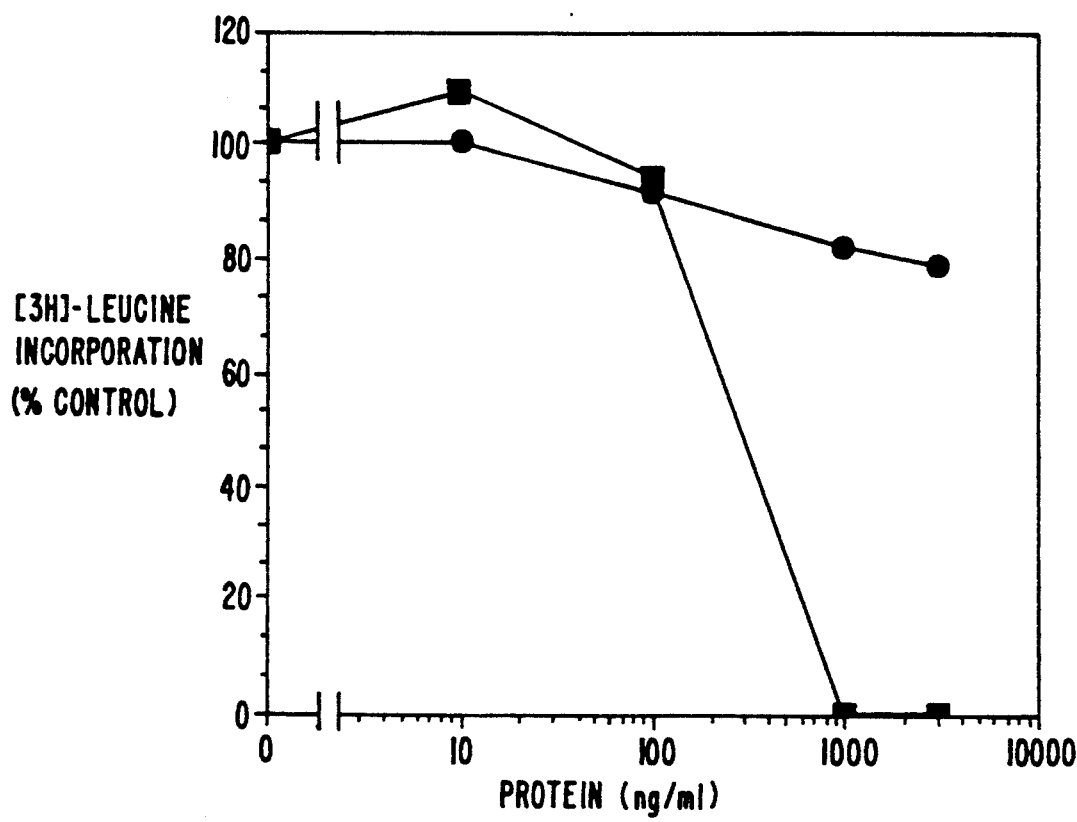

Cell line 103-PE ® is a PE-resistant hybridoma that contains a mutant EF-2 that cannot be ADP-ribosylated by PE and therefore is resistant to the cytotoxic activity of PE. Since cell line 103 is a thymidine-uptake negative strain, cytotoxicity was evaluated using [$^3$H]-leucine. As shown in FIG. 6, cell line 103, the PE-sensitive parent of 103-PE ®, was sensitive to the toxins PE and PE-Bar. Conversely, cell line 103-PE ® was sensitive only to PE-Bar; PE had no effect on cell line 103-PE ®. This result supports the conclusion that the barnase moiety is functional and active in target cells.

In summary, the evidence presented herein demonstrates for the first time a successful construction of a series of chimeric toxins by fusing the DNA encoding mature *B. amyloliquefaciens* barnase, to a gene encoding PE. This hybrid toxin was produced by *E. coli* and purified from this source. The fusion protein, termed PE-Bar, reacted with both anti-PE and anti-barnase antisera. Further, the chimeric toxin displayed both ADP-ribosylation and ribonuclease activities derived from the PE and barnase moieties, respectively. PE-Bar was cytotoxic to the murine fibroblast cell line L929 and to a murine hybridoma resistant to PE.

Several lines of evidence indicated that the cytotoxic action of PE-Bar is due to its nuclease activity which has been translocated to the cytosol:

(a) a derivative of PE-Bar (PE$^{\Delta 553\text{-}Bar}$) in which the glutamic acid residue at position 553 of PE necessary for ADP-ribosylation (Douglas and Collier, 1987, J. Bacteriol. 169:4967–4971) was deleted, was still cytotoxic to cells;

(b) PE-Bar was toxic to a PE resistant cell line with a mutant elongation factor-2 that cannot be ADP-ribosylated and inactivated by PE;

(c) the chimeric toxin PE-Bar-COOH which lacks the carboxyl amino acids of PE (609–613) necessary for translocation of a 37 kD fragment of PE into the cytosol (Chaudhary et al, 1990, supra) was not active;

(d) Ribonuclease activity was present in the cytosol and decreased the amount of uridine labeled RNA in cells treated with barnase containing fusion proteins, but not with PE itself.

The results presented here remarkably show that chimeric proteins containing in part a foreign polypeptide which is normally impermeable to cells, can now be made and delivered to the cytosol in functionally intact form. The polypeptide may, of course, have cytotoxic, therapeutic, diagnostic, or any other desired activity. For example, peptides which usually bind to the cell surface via MHC Class II interactions can be introduced into the cytosol of the presenting cell and given the opportunity to interact with the Class I pathway. Furthermore, if PE were to be used as a translocating vehicle, domain Ia which binds to all cells as a targeting domain, can be replaced with growth factors, antigens, lymphokines, single chain antibodies and the like or with other suitable cell recognition molecules for targeting to specific cells in vitro or in vivo.

Of course, chimeric proteins containing a variety of foreign proteins in accordance with the present invention can now be made following the method similar to that described herein for PE-Bar and the like. A few examples are further illustrated.

Figure 7A:
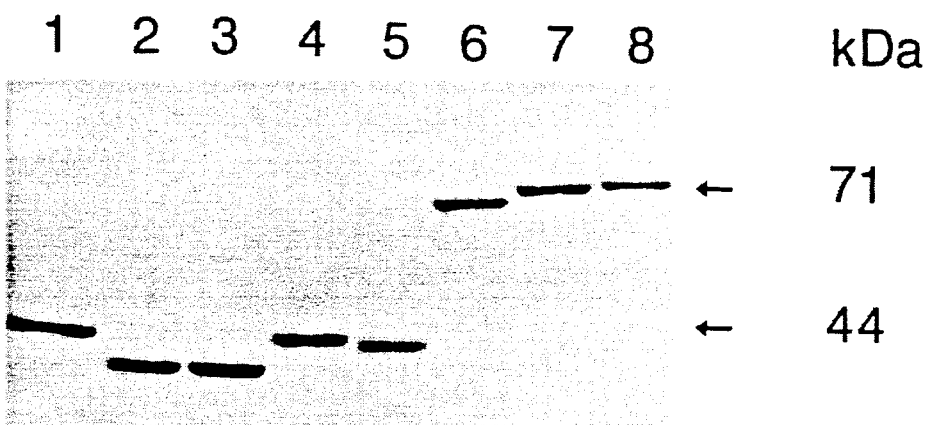
Figure 7B:
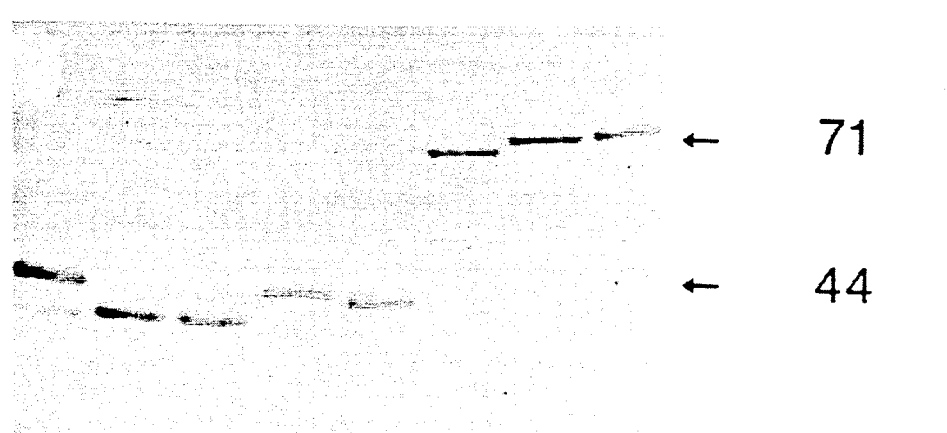
Figure 7C:
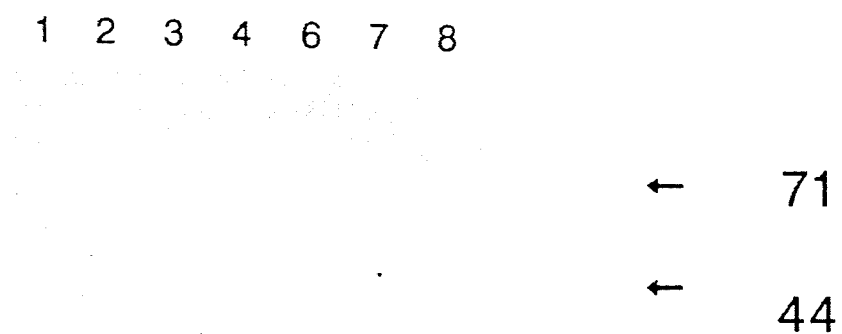

Cytotoxic and ADP-ribosylating activities of chimeric toxins with substitutions of somatostatin and a methionine-rich peptide. The plasmids, their encoded chimeric proteins, their molecular weights and cytotoxicities are shown in FIG. 8. Toxicity was measured as inhibition of [$^3$H] leucine incorporation into cellular proteins in the presence of various derivatives of chimeric toxin (Hwang et al, 1987, Cell 48:129–136). ADP-ribosylation activity was assayed according to the method of Collier and Kandel (Collier and Kandel, 1971, J. Biol. Chem. 246:1496–1503). Protein concentration was estimated by the Bradford assay using the Pierce (Rockford, Ill.) Coomassie-Blue G-250 based reagent. To determine purity, chimeric toxins were analyzed by SDS-polyacrylamide gel electrophoresis, as shown in FIG. 7. All the purified proteins exhibited the expected molecular weights (FIG. 7a; see also FIG. 8) and their purity was greater than 90%. Immunoreactivity of Western blots with a polyclonal antibody to PE revealed bands corresponding to the Coomassie-Blue stained protein bands (FIG. 7b). TGFα-PE40 derivatives which had different versions of somatostatin-14 inserted into domain Ib (FIG. 7c, lane 2 and 3) were identified by an anti-somatostatin antibody; this antibody did not react with any other of the TGFα-PE40 toxins. Proteins reacting with anti-PE or anti-somatostatin antibodies were identified with a Vecta-Stain kit (Vector Laboratories, Burlingame, Calif.). As shown, protein synthesis inhibition assays were carried out on A431 and HT29 cell lines, both being sensitive to TGFα-PE40 (Siegall et al, 1989, FASEB J. 3:2647–2652). The results are presented as the concentration that produces a 50% reduction in protein synthesis (ID$_{50}$). TGFα-PE40 had an ID$_{50}$ of 7 pM on A431 cells and 43 pM on HT29 cells. The two chimeric toxins containing somatostatin-14 with or without cysteines were also active and demonstrated similar activities to TGFα-PE40 on both cell lines. In addition, they had similar ADP-ribosylation activities (77 and 89% of TGFα-PE40 activity, respectively; 100%=102 cpm/ng/15 min). The cytotoxic activity of a fusion protein containing a peptide enriched in methionine residues (56% of the inserted amino acids) was also very close to that exhibited by TGFα-PE40. These findings show that foreign amino acid sequences can be introduced into the toxin structure while keeping intact the membrane translocation and cytotoxic activities. It is noted that TGFα-PE40Asp$^{553}$ did not have any activity on HT29 cells and had very weak cytotoxic activity (ID$_{50}$=4 nM) on A431 cells.

From the studies presented herein and from the work carried out in our laboratories, we hypothesize without being bound to any specific theory that, in order to be active, the toxin has to be proteolytically cleaved within domain II (Ogata et al, 1990, supra) and a proper C-terminal sequence appears necessary for the hybrid molecule to possess full cytotoxicity. Without being bound to any specific postulate, it is further deduced from the studies presented herein, where the constructions had one intact domain II and a normal C-terminal end of PE40, that any changes made in the Ib region should not influence the process of proteolysis or C-terminal recognition.

From the various examples illustrated herein, clearly it now becomes possible to introduce specific peptides, enzymes, single chain antibodies and the like into the cell cytoplasm using at least PE or its derivatives and hybrids. By making such molecules without ADP-ribosylating activity and leaving the other features of domain II and the C-terminus of PE unchanged, insertion into domain Ib may be an efficient way to accomplish this goal. In fact, the fusion protein which had a mutated domain III distal to a normal domain III (see for example pWD151 in FIG. 8) serves as a typical example of such an approach. Of course, in order to translocate other sequences into the cytosol, in accordance with one aspect of the present invention, the nucleotide sequence for barnase is simply replaced with a DNA sequence that encodes the desired protein or polypeptide which needs to be translocated in the cytosol. For instance, to make a new toxin, barnase would be replaced with a new toxic moiety; to make a new marker protein, barnase sequence would be replaced with the desired marker sequence and so on. Of course, given the examples described herein, one of ordinary skill in the art can now construct any desired recombinant DNA molecule for translocating a foreign protein into the cytosol of a target cell by otherwise well known techniques of genetic engineering such as described in Maniatis et al, A manual of Molecular Cloning, Coldspring Harbor, N.Y., 1982.

It is understood that the examples described herein are only illustrative and that various modifications or changes in light thereof will be suggested to persons skilled in the art and are to be included within the spirit and purview of this application and scope of the appended claims.

TABLE 1

Enzymatic Activity of the Chimeric Toxins

| Protein | Relative Activity (% control) | |
|---|---|---|
| | ADP-Ribosylation[a] | Ribonuclease[b] |
| PE | 100 | <0.1 |
| Barnase | N.D.[c] | 100 |
| PE-Bar | 90 | 80 |
| PE$^{\Delta 553}$-Bar | 0 | 50 |
| PE-Bar-COOH | 80 | 70 |

[a]ADP-ribosylation was measured using 140 ng of protein in a final volume of 0.25 ml. Results are expressed as a percentage of the activity observed with PE.
[b]Ribonuclease activity was calculated as the amount of polyethenoadenosine phosphate degraded per minute per mole of protein. Results are expressed as a percentage of the activity observed with barnase.
[c]Not done.

TABLE 2

Cytotoxic Activity of the Chimeric Toxins on L929 Cells

| Protein | [$^3$H]-Leucine Incorporation | [$^3$H]-Thymidine Incorporation | |
|---|---|---|---|
| | 48 hr ID$_{50}$ (ng/ml) | 24 hr ID$_{50}$ (ng/ml) | 48 hr ID$_{50}$ (ng/ml) |
| PE | 0.03 | N.D.[a] | 0.05 |
| PE$^{\Delta 553}$ | >1000 | N.D. | >1000 |
| PE-Bar | 5 | 9 | 2 |
| PE$^{\Delta 553}$-Bar | 60 | 150 | 90 |
| PE-Bar-COOH | N.D. | >1000 | >1000 |

Assays were performed after the indicated time of incubation with toxin. ID$_{50}$ is the protein concentration required to inhibit [$^3$H]-leucine or [$^3$H]-thymidine incorporation by 50%.
(a) Not Done.

TABLE 3

DNA Primers Used in This Study

| Primer 1 (SEQ ID NO:5) | 5'CTG TTT ACC CCT GTG ACA CAT ATG GCA CAG GTT ATC AAC ACG3' |
| Primer 2 (SEQ ID NO:6) | 5'AAT TTA TTA CAC ACT GTG CAC TTA TTA CTT AAG GTC CTC GCG CGG AGG TTT CCC GGG CTG GCT GGC TCT GAT TTT TGT AAA3' |
| Primer 3 (SEQ IN NO:7) | 5'AAC TGA TAG AAT AAA GTG CAC AGA AAG AGG CCG CAC ATG AAA AAA G3' |
| Primer 4 (SEQ ID NO:8) | 5'GTT CAT CTC CCA TTG GAA TTC TTA AGA AAG TAT GAT G3' |
| Primer 5 (SEQ ID NO:9) | 5'GGC CTC CGC AGG AAG GTG CAC GAG CTC TTA TCT GAT TTT TGT AAA GGT3' |
| Primer 6 (SEQ ID NO:10) | 5'GAG GAA GGC GGG CGC CTG ACC ATT CTC GGC TGG CCG3' |
| Primer 7 (SEQ ID NO:11) | 5'ATT TTC AGT CAG CTG CTT G3' |

Oligonucleotides were prepared and used as discussed in Materials and Methods.

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( v ) FRAGMENT TYPE: internal ( v i ) ORIGINAL SOURCE:
        ( A ) ORGANISM: Pseudomonas aeruginosa ( x ) PUBLICATION INFORMATION:
        ( A ) AUTHORS: Debinski, Waldemar
                    Siegall, Clay B.
                    FitzGerald, David
                    Pastan, Ira
        ( B ) TITLE: Substitution of Foreign Protein Sequences
                into a Chimeric Toxin Composed of Transforming
                Growth Factor alpha and Pseudomonas Exotoxin
        ( C ) JOURNAL: Mol. Cell. Biol.

(D) VOLUME: 11
(E) ISSUE: 3
(F) PAGES: 1751-1753
(G) DATE: March-1991

(xi) SEQUENCE DESCRIPTION: SEQ ID NO:1:

Ala Asp Val Val Ser Leu Thr Cys Pro Val Ala Ala Gly Glu Cys Ala
1               5                   10                  15

(2) INFORMATION FOR SEQ ID NO:2:

(i) SEQUENCE CHARACTERISTICS:
    (A) LENGTH: 14 amino acids
    (B) TYPE: amino acid
    (D) TOPOLOGY: linear (ii) MOLECULE TYPE: peptide (xi) SEQUENCE DESCRIPTION: SEQ ID NO:2:

Thr Gly Cys Lys Asn Phe Phe Trp Lys Thr Phe Thr Ser Cys
1               5                   10

(2) INFORMATION FOR SEQ ID NO:3:

(i) SEQUENCE CHARACTERISTICS:
    (A) LENGTH: 14 amino acids
    (B) TYPE: amino acid
    (D) TOPOLOGY: linear (ii) MOLECULE TYPE: peptide (xi) SEQUENCE DESCRIPTION: SEQ ID NO:3:

Thr Gly Ser Lys Asn Phe Phe Trp Lys Thr Phe Thr Ser Ser
1               5                   10

(2) INFORMATION FOR SEQ ID NO:4:

(i) SEQUENCE CHARACTERISTICS:
    (A) LENGTH: 16 amino acids
    (B) TYPE: amino acid
    (D) TOPOLOGY: linear (ii) MOLECULE TYPE: peptide (xi) SEQUENCE DESCRIPTION: SEQ ID NO:4:

Met Asp Met Met Met Met Thr Cys Pro Met Met Gly Thr Cys Met
1               5                   10                  15

(2) INFORMATION FOR SEQ ID NO:5:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:5:

CTGTTTACCC CTGTGACACA TATGGCACAG GTTATCAACA CG                                  42

(2) INFORMATION FOR SEQ ID NO:6:

(i) SEQUENCE CHARACTERISTICS:
    (A) LENGTH: 81 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:6:

```
AATTTATTAC ACACTGTGCA CTTATTACTT AAGGTCCTCG CGCGGAGGTT TCCCGGGCTG        60

GCTGGCTCTG ATTTTTGTAA A                                                 81
```

(2) INFORMATION FOR SEQ ID NO:7:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
AACTGATAGA ATAAAGTGCA CAGAAAGAGG CCGCACATGA AAAAG                       46
```

(2) INFORMATION FOR SEQ ID NO:8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
GTTCATCTCC CATTGGAATT CTTAAGAAAG TATGATG                                37
```

(2) INFORMATION FOR SEQ ID NO:9:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GGCCTCCGCA GGAAGGTGCA CGAGCTCTTA TCTGATTTTT GTAAAGGT                    48
```

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
GAGGAAGGCG GGCGCCTGAC CATTCTCGGC TGGCCG                                 36
```

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
ATTTTCAGTC AGCTGCTTG                                                    19
```

What is claimed is:

2. The chimeric protein of claim 1, wherein said third segment is a ligand, an antibody, a growth factor or a cytokine for selective recognition of target cells.

3. The chimeric protein of claim 1, being PE-Bar.

4. The chimeric protein of claim 1, being PE$^{\Delta 553}$-Bar.

5. A DNA molecule having a sequence that encodes the chimeric protein of claim 1.

6. A method for introducing a foreign protein across a cellular membrane into the cytosol of target cells, comprising the step of contacting cells into which a foreign protein is desired to be introduced, with the chimeric protein of claim 1.

7. A composition comprising an effective amount of the chimeric protein of claim 1 and pharmaceutically acceptable carrier.

8. A chimeric protein comprising:
a first segment comprising a foreign protein;
a second segment from Domain II of Pseudomonas exotoxin which translocates the first segment across a cellular membrane; and
a third segment which binds the chimeric protein to a target cell;
wherein the foreign protein is heterologous to the second segment.

9. The chimeric protein of claim 8, wherein the third segment is a ligand, an antibody, a growth factor or a cytokine.

10. The chimeric protein of claim 8, wherein the third segment is Domain Ia of Pseudomonas exotoxin.

11. The chimeric protein of claim 8, wherein the foreign protein is selected from the group consisting of barnase and somatostatin.

12. A DNA molecule sequence that encodes a chimeric protein having a foreign protein segment, a segment from Domain II of Pseudomonas exotoxin that has a translocation function which delivers the foreign protein across cellular membranes into the cytosol of target cells all linked to a third segment which encodes a protein that binds the chimeric protein to the target cells, the foreign protein being otherwise impermeable to the target cells and heterologous to the protein having the translocation function.

13. A method of making a translocatable chimeric protein, comprising the step of making a chimeric gene by linking together at least (1) a foreign protein gene sequence that encodes a foreign protein desired to be introduced into the cytosol of a target cell, (2) a heterologous gene sequence from a sequence encoding Domain II of Pseudomonas exotoxin that encodes a protein having a translocation function which delivers the foreign protein across the cellular membrane into the cytosol of the target cell, and (3) a gene sequence encoding a protein which binds the chimeric protein to the target cell, then allowing the expression of said chimeric gene in a suitable expression system so that a translocatable chimeric protein is obtained, and then recovering said chimeric protein from said expression system.

* * * * *

UNITED STATES PATENT AND TRADEMARK OFFICE
CERTIFICATE OF CORRECTION

PATENT NO. : 5,328,984

DATED : July 12, 1994

INVENTOR(S) : Ira H. Pastan, Trevor Prior, David J. Fitzgerald, Waldemar Debinski, Clay Siegall It is certified that error appears in the above-identified patent and that said Letters Patent is hereby corrected as shown below:

Cover sheet, item [75] Inventors: delete "Prior Trevor, Bethesda" and insert therefor --Trevor Prior, Calgary, Alberta, Canada--.

Column 19, line 1, before Claim 2 insert Claim 1 as follows:

--1. A chimeric protein of which a portion is translocated across a cellular membrane into the cytosol of target cells, the chimeric protein comprising, linked together at least (1) a first segment comprising a foreign protein desired to be introduced into the cytosol of the target cells, (2) a second segment from Domain II of Pseudomonas exotoxin having a translocation function which delivers the foreign protein across the cellular membrane into the cytosol of the target cells, and (3) a third segment which binds the chimeric protein to the target cells the foreign protein being otherwise impermeable to the target cells and heterologous to the second segment.--

Signed and Sealed this

Eighth Day of November, 1994

Attest:

BRUCE LEHMAN

Attesting Officer

Commissioner of Patents and Trademarks